United States Patent [19]

Farrenkopf et al.

[11] 4,112,064
[45] Sep. 5, 1978

[54] STABILIZED ANGIOTENSIN I SOLUTIONS

[75] Inventors: Bruce Charles Farrenkopf, Clifton; Magdalena Usategui Gomez, Wayne, both of N.J.

[73] Assignee: Hoffmann-La Roche Inc., Nutley, N.J.

[21] Appl. No.: 770,335

[22] Filed: Feb. 22, 1977

[51] Int. Cl.$^2$ .................. A61K 43/00; G01N 33/16
[52] U.S. Cl. .................. 424/1; 23/230 B; 424/12
[58] Field of Search .................. 424/1, 1.5, 12; 23/230 B

[56] References Cited

U.S. PATENT DOCUMENTS 3,843,775   10/1974   Wolf .................. 424/1
3,899,298   8/1975   Szczesniak .................. 23/230 B X
3,984,532   10/1976   Fernandez de Castro .................. 424/12 X Primary Examiner—Benjamin R. Padgett
Assistant Examiner—Christine M. Nucker
Attorney, Agent, or Firm—George M. Gould; Samuel L. Welt; George M. Gould

[57] ABSTRACT

Angiotensin I and iodinated angiotensin I solutions are stabilized against enzymatic degradation by the addition of phenylmethylsulfonyl fluoride (PMSK). Such solutions are used as standards and reagents in immunoassay kits for determinatin of plasma renin levels. Stabilized solutions prepared in accordance with this disclosure can be shipped at ambient temperature which represents a substantial advantage in convenience over previously available solutions of angiotensin I and radioiodinated angiotensin I.

10 Claims, No Drawings

STABILIZED ANGIOTENSIN I SOLUTIONS

BACKGROUND OF THE INVENTION

Angiotensin I stability (whether the peptide is iodinated or not) in buffer solutions containing protein and preservatives (i.e., sodium azide and/or ethylenediamine tetraacetic acid (EDTA)) has been a serious problem for many years. It is common practice in the art to keep angiotensin I solutions frozen at −20° C prior to use since even at refrigerator temperatures the peptide can be destroyed by proteases in a few days. At room temperature the peptide will last approximately 24 hours.

Thus all presently available preparations of angiotensin I or radioiodinated angiotensin I are shipped frozen or are lyophilized. Upon arrival, when shipped frozen, the package instructions call for aliquotting and storage at −20° C or storage of the entire material at −20° C with a limited number of defrosting and freezing cycles.

Lyophilized material has the practical drawback of requiring reconstitution before use. Moreover, the package instructions for storage after reconstitution vary from storge at 4° C for 2 months to thawing of reconstituted vials stored at −20° C as needed and thereafter storage at 4° C.

It has been known in the art to add PMSF to plasma samples undergoing assay for renin activity as a means for maximizing the production of angiotensin I during the assay by preventing loss of this compound through side reactions. See in this regard U.S. Pat. Nos. 3,919,407 and 3,984,352. However, the angiotensin I standards and $^{125}$I angiotensin I are indicated in these patents to be derived from a commercial kit thereby implying that they were stabilized in accordance with prior art procedures as discussed above.

DESCRIPTION OF THE INVENTION

It has now been discovered that highly stable solutions of angiotensin I and radioiodinated angiotensin I can be obtained by incorporating phenylmethylsulfonyl fluoride into the buffer solutions employed to dilute these substances in conjunction with the conventionally employed stabilizers, i.e. sodium azide and ethylenediamine tetraacetic acid (EDTA), usually in the form of the sodium salt. The improvement in stability over the prior art stabilizers is substantial. Compositions prepared in accordance with the present invention can be shipped at ambient temperature thus saving the expense and bother of special packaging and handling required for frozen shipments. Additionally, such compositions can be stored at 4° C for the life of the assay kit and can be used in an assay conducted at room temperature thereby avoiding running the assay over ice as required by prior art assay systems. Furthermore, the compositions are ready for immediate use without the need of thawing or reconstitution.

It has further been found that PMSF can stabilize solutions of polypeptides and proteins. Examples of such polypeptides and proteins include gamma globulins, serum albumins, antigens, antibodies, enzymes other than proteases or peptidases and the like. The quantities of PMSF used will generally follow those utilized in the Angiotensin I and radioiodinated angiotensin I embodiments disclosed herein.

The compositions of the present invention comprise angiotensin I 0.1 ng to 10 mg and radioiodinated angiotensin in an amount in the range of 1 pg to 1000 ng dissolved in 1 ml of a conventional buffer system such as 0.1 M Tris buffer pH 7.5 for the standard and 0.1 M Tris pH 9.0 for the label to which has been added from 0.1 to 10 mg of sodium azide, from 0.1 mg to 2 mg of the sodium salt of ethylenediamine tetracetic acid, 0.1 mg to 50 mg of carrier protein such as a bovine serum albumin and from 0.01 to 5 mg of phenylmethylsulfonyl fluoride.

It is also possible to introduce a precipitation enhancing protein to aid in the subsequent separating step in the radioimmunoassay. Such proteins include gamma globulins such as bovine gamma globulin. A particularly preferred embodiment of the subject composition of the present invention contains the following:

0.1 M Tris buffer pH 7.5; 1 ml
angiotensin I; 10 ng
Sodium azide; 1.0 mg
Na EDTA; 1.1 mg
PMSF; 1.3 mg
Bovine serum albumin; 3 mg
0.1 M Tris buffer pH 9.0; 1 ml
$^{125}$I angiotensin I; 50 pg
Sodium azide; 1.0 mg
Na EDTA; 1.1 mg
PMSF; 1.3 mg
Bovine serum albumin; 3 mg After the compositions have been mixed together excluding at this point Angiotensin I or radioiodinated Angiotensin, it is necessary to heat the mixture at 55°–60° C. for about 15 minutes. This serves to assist the solubilization of the PMSF and also is desirable to inactivate any peptidases that may be present. In the case of the radiolabelled composition the initial pH adjustment is to pH 8.0 prior to heating and then a final adjustment to pH 9.0 is made after cooling. The peptides are then added to the cooled solutions.

The increase in stability obtained by adding PMSF to stabilized, buffered solutions of angiotensin I and $^{125}$I-angiotensin I is clearly demonstrated in the results of stability experiments carried out therein.

Tables 1 through 4 below summarize the results of comparison tests between the PMSF containing compositions of the present invention and compositions containing the prior art stabilizers (sodium azide, EDTA). The general testing procedure utilized to generate these results is as follows:

GENERAL TESTING PROCEDURE

I. Reagents for Radioimmunoassay
  A. $^{125}$I-Angiotensin I Reagents: $^{125}$I-Angiotensin I, 0.3% Bovine Serum Albumin and 0.5% Bovine Gamma Globulin in 0.1 M Tris-Acetate Buffer (pH 9.0) with sodium azide, EDTA and PMSF.
  B. Angiotensin I Standards: Angiotensin I diluted to 1.0, 2.5, 5.0, 10, 20 and 50 ng/ml concentrations with 0.3% Bovine Serum Albumin in 0.1 M Tris-Acetate Buffer (pH 7.5) with sodium azide, EDTA and PMSF.
  C. Angiotensin I Antiserum: Angiotensin I Antiserum (rabbit), 0.3% Bovine Serum Albumin in 0.1 M Tri-Acetate Buffer (pH 7.5) with sodium azide, EDTA and PMSF.
  D. Polyethylene Glycol: 15% Polyethylene Glycol in 0.01 M Tris-Acetate Buffer (pH 7.0).

II. Radioimmunoassay

The radioimmunoassay was conducted in duplicate employing 12 × 75 mm polystyrene test tubes. The assay was set up at room temperature.

A. A series of polystyrene tubes were marked with the numbers 1 through 18 to be used for the preparation of the standard curve.

B. A 200 microliter aliquot of $^{125}$I-Angiotensin I Reagent was added to all test tubes.

C. A 20 microliter aliquot of each Angiotensin I Standard was added to the appropriate tubes, i.e. 1.0 ng/ml standard into tubes 7 and 8, 2.5 ng/ml standard into tubes 9 and 10 etc.

D. A 20 microliter aliquot of Angiotensin I Antiserum was added to tubes 5 through 18.

E. The tubes were vortexed and covered loosely with a paper towel.

F. The tubes were equilibrated for 1 hour ± 5 minutes at room temperature.

G. At the end of the equilibration period, 2.0 ml of cold Polyethylene Glycol Solution was added to tubes 3 through 18.

H. The tubes were vortexed thoroughly and placed at 4° C. for 10 minutes.

I. The tubes were centrifuged at 4° C. and 3500 × g for 10 minutes.

J. The supernatant of tubes 3 through 18 was decanted off by inverting the tubes. The tubes were allowed to drain in the inverted position for 5 minutes.

K. The radioactivity of the total count tubes (tubes 1 and 2) and the pellets was counted for 1 minute in a gamma scintillation counter.

Table I

STABILITY OF $^{125}$I-ANGIOTENSIN I REAGENT
% Difference* From Zero Day

| | | Sodium Azide | | | | | | | Sodium Azide + EDTA | | | | | | | | Sodium Azide + EDTA + PMSF | | | | | | | |
|---|---|---|---|---|---|---|---|---|---|---|---|---|---|---|---|---|---|---|---|---|---|---|---|---|
| | | 4° C | | | | | 25° C | | 4° C | | | | | 25° C | | | 4° C | | | | | 25° C | | |
| Temp. Time | OD | 1W | 2W | 1M | 2M | 3M | 1W | 2W | 1M | OD | 1W | 2W | 1M | 2M | 3M | 1W | 2W | 1M | OD | 1W | 2W | 1M | 2M | 3M | 1W | 2W | 1M |
| Angiotensin Standards 0 pg | 0% | 3.1% | — | 17.4% | 29.2% | 45.0% | — | — | 48.2% | 90.4% | 0% | 5.8% | 2.5% | 2.1% | 8.6% | 3.9% | 4.5% | 6.8% | 6.6% | 0% | 2.9% | 0.7% | 1.8% | 0.0% | 1.1% | 2.4% | 4.2% | 4.2% |
| 20 | 0 | 5.4 | — | 18.4 | 29.7 | 41.4 | — | — | 46.2 | 91.1 | 0 | 4.9 | 0.5 | 3.3 | 2.7 | 1.0 | 5.6 | 6.1 | 6.6 | 0 | 4.1 | 4.1 | 4.1 | 0.6 | 6.1 | 0.3 | 0.3 | 1.4 |
| 50 | 0 | 3.9 | — | 22.8 | 31.1 | 44.0 | — | — | 54.2 | 93.1 | 0 | 1.0 | 0.6 | 8.2 | 3.0 | 5.0 | 7.4 | 1.3 | 1.9 | 0 | 0.0 | 2.4 | 2.4 | 4.1 | 4.1 | 1.1 | 3.6 | 3.9 |
| 100 | 0 | 0.9 | — | 25.0 | 28.9 | 42.2 | — | — | 52.6 | 85.3 | 0 | 5.8 | 4.7 | 10.1 | 6.9 | 1.3 | 5.2 | 5.2 | 7.3 | 0 | 4.6 | 4.2 | 4.2 | 1.0 | 1.0 | 2.4 | 0.5 | 2.4 |
| 200 | 0 | 4.6 | — | 25.6 | 28.9 | 46.0 | — | — | 55.9 | 88.2 | 0 | 9.0 | 3.2 | 5.4 | 4.3 | 0.6 | 5.1 | 7.0 | 4.5 | 0 | 4.0 | 0.7 | 1.4 | 6.7 | 5.7 | 4.7 | 4.7 | 6.8 |
| 300 | 0 | 12.7 | — | 31.7 | 34.5 | 45.5 | — | — | 57.8 | 88.7 | 0 | 10.3 | 7.9 | 2.3 | 7.1 | 5.5 | 7.2 | 11.9 | 10.3 | 0 | 0.9 | 1.7 | 1.7 | 8.6 | 2.5 | 3.3 | 6.0 | 8.6 |
| 500 | 0 | 7.7 | — | 21.2 | 25.0 | 44.4 | — | — | 58.0 | 92.5 | 0 | 12.2 | 5.7 | 6.8 | 1.2 | 3.5 | 2.4 | 6.1 | 4.9 | 0 | 6.0 | 3.6 | 11.9 | 9.5 | 7.7 | 10.7 | 3.4 | 2.4 |

Key to Abbreviations:
° C — Degrees Centigrade
EDTA — Ethylenediamine Tetraacetate
PMSF — Phenylmethylsulfonyl Fluoride
Pg — Picograms ($10^{-12}$ grams)
OD — Zero Day
W — Week
M — Month Summary of Stability

| | 4° C | 25° C |
|---|---|---|
| Sodium Azide | 1 week | <1 week |
| Sodium Azide + EDTA | <3 months | >1 month |
| Sodium Azide + EDTA + PMSF | >3 months | >1 month |

Stability Specifications: Stability was considered lost if three or more experimental values had a % difference greater than 15% from the corresponding zero day values.

*% Difference = $\left[1 - \left(\frac{\text{smaller}}{\text{larger value}}\right)\right] \times 100$ Table II STABILITY OF ANGIOTENSIN I STANDARDS
% Difference* from Control

| | | Sodium Azide | | | | | | | | | Sodium Azide + EDTA | | | | | | | | Sodium Azide + EDTA + PMSF | | | | | | | | | | |
|---|---|---|---|---|---|---|---|---|---|---|---|---|---|---|---|---|---|---|---|---|---|---|---|---|---|---|---|---|---|
| | | 4°C | | | | | | 25°C | | | 4°C | | | | 25°C | | | | 4°C | | | | | | 25°C | | | | |
| | Temp. Time | OD | 1W | 2W | 1M | 2M | 3M | 1W | 2W | 1M | OD* | 1W | 2W | 1M | 1W | 2W | 1M | | OD | 1W | 2W | 1M | 2M | 3M | 1W | 2W | 1M | 2M |
| Angiotensin standards | 20pg | 0.0% | 3.8% | — | 8.9% | 10.0% | 8.2% | 8.8% | — | 16.7% | 5.0% | 1.3% | 12.6% | 5.4% | 2.8% | 13.9% | 13.1% | | 2.7% | 1.7% | 2.0% | 3.9% | 5.3% | 0.6% | 0.5% | 1.5% | 5.9% | 5.4% |
| | 50 | 4.0 | 6.3 | — | 11.1 | 21.0 | 21.8 | 17.6 | — | 29.9 | 1.5 | 5.8 | 16.3 | 9.4 | 13.1 | 25.7 | 21.8 | | 3.4 | 0.3 | 3.4 | 5.5 | 1.1 | 3.0 | 1.8 | 2.6 | 12.6 | 1.2 |
| | 100 | 4.8 | 13.1 | — | 14.3 | 22.8 | 30.0 | 26.9 | — | 45.7 | 8.6 | 9.7 | 15.9 | 16.5 | 21.7 | 31.3 | 38.3 | | 1.7 | 2.5 | 3.5 | 9.6 | 1.9 | 8.5 | 6.8 | 3.8 | 7.0 | 1.9 |
| | 200 | 1.8 | 13.7 | — | 23.1 | 31.5 | 34.1 | 27.4 | — | 58.7 | 0.6 | 1.1 | 12.1 | 14.3 | 10.4 | 24.8 | 44.6 | | 0.0 | 1.3 | 3.4 | 4.9 | 2.3 | 0.6 | 3.3 | 0.0 | 23.5 | 6.7 |
| | 300 | 4.3 | 12.7 | — | 23.2 | 25.4 | 44.7 | 34.7 | — | 68.1 | 12.6 | 11.6 | 12.4 | 16.1 | 16.4 | 19.1 | 39.5 | | 1.6 | 11.0 | 3.0 | 8.8 | 14.5 | 0.7 | 9.8 | 3.8 | 3.9 | 8.7 |
| | 500 | 4.6 | 20.1 | — | 29.5 | 24.6 | 42.6 | 34.1 | — | 62.3 | 7.9 | 4.3 | 7.4 | 13.4 | 19.3 | 27.5 | 47.6 | | 1.2 | 14.0 | 6.7 | 1.4 | 13.2 | 3.3 | 12.0 | 8.7 | 5.5 | 13.2 |

Key to Abbreviations:
°C     — Degrees Centigrade
EDTA  — Ethylenediamine Tetraacetate
PMSF  — Phenylmethylsulfonyl Fluoride
pg    — Picograms (10⁻¹² grams)
OD    — Zero Day
W     — Week
M     — Month Summary of Stability

| | 4° C | 25° C |
|---|---|---|
| Sodium Azide | <1 week | <1 week |
| Sodium Azie | 1 week | <1 week |
| Sodium Azie + EDTA + PMSF | >3 months | >2 Months |

Stability Specifications: Stability was considered lost if three or more experimental values has a % difference greater than 10% from the corresponding control values.

*% Difference = $\left[1 - \left(\dfrac{\text{smaller}}{\text{larger value}}\right)\right] \times 100$

Table III

STABILITY OF $^{125}$I-ANGIOTENSIN I REAGENT
% Difference* From Control

| | | Sodium Azide + EDTA + PMSF | | | | | | | | | | | | | | | | | | | | |
|---|---|---|---|---|---|---|---|---|---|---|---|---|---|---|---|---|---|---|---|---|---|---|
| | | −15° C | | | | | 4° C | | | | | 25° C | | | | | 37° C | | | 45° C |
| | Temp. Time | 2W | 1M | 2M | 3M | 4M | 2W | 1M | 2M | 3M | 4M | 2W | 1M | 2M | 3M | 4M | 2W | 1M | 2M | 2W |
| Angio-tensin standards | 0 pg | 0 | 0.4% | 2.6% | 3.4% | 6.6% | 4.3% | 1.0% | 2.6% | 4.5% | 6.4% | 3.3% | 3.9% | 6.8% | 12.5% | 16.1% | 0.8% | 9.0% | 10.6% | 8.8% |
| | 20 | 0 | 0.0 | 5.7 | 4.6 | 3.1 | 8.7 | 1.2 | 0.3 | 3.3 | 8.2 | 2.4 | 2.0 | 7.5 | 12.8 | 14.0 | 2.2 | 8.5 | 13.4 | 7.3 |
| | 50 | 0 | 2.3 | 6.0 | 0.3 | 3.7 | 7.0 | 3.7 | 1.6 | 0.3 | 4.0 | 3.3 | 1.4 | 9.2 | 8.2 | 17.3 | 2.8 | 11.5 | 15.9 | 7.9 |
| | 100 | 0 | 4.2 | 5.4 | 3.4 | — | 6.7 | 1.1 | 1.3 | 0.8 | — | 6.7 | 1.3 | 10.3 | 7.6 | — | 3.6 | 7.0 | 16.7 | 6.3 |
| | 200 | 0 | 2.0 | 8.4 | 6.9 | 1.7 | 7.2 | 5.7 | 2.9 | 1.1 | 1.2 | 6.3 | 0.7 | 11.9 | 10.9 | 13.9 | 5.3 | 15.3 | 18.6 | 15.0 |
| | 400 | 0 | 0.6 | 4.4 | 1.0 | 2.0 | 5.0 | 3.5 | 0.6 | 9.6 | 3.9 | 7.0 | 9.9 | 5.1 | 9.6 | 0.0 | 1.8 | 18.3 | 5.9 | 19.7 |
| | 1000 | 0 | 12.4 | 8.8 | 15.5 | 2.2 | 27.1 | 13.3 | 8.8 | 12.1 | 19.6 | 11.1 | 8.4 | 13.8 | 5.2 | 13.3 | 1.8 | 21.1 | 11.4 | 23.7 |

Summary of Stability

| Temp. | Time |
|---|---|
| −15° C | 4 months |
| 4° C | 4 months |
| 25° C | 4 months |
| 37° C | 1 month |
| 45° C | 2 weeks |

Key to Abbreviations:

| | | |
|---|---|---|
| ° C | — | Degrees Centigrade |
| EDTA | — | Ethylenediamine Tetraacetate |
| PMSF | — | Phenylmethylsulfonyl Fluoride |
| pg | — | Picograms ($10^{-12}$ grams) |
| OD | — | Zero Day |
| W | — | Week |
| M | — | Month |

Stability Specifications: Stability was considered lost if three or more experimental values had a % difference greater than 15% from the corresponding control values.

*% Difference = $\left[1 - \left(\dfrac{\text{smaller value}}{\text{larger value}}\right)\right] \times 100$ Table IV STABILITY OF ANGIOTENSIN I STANDARDS
% Difference* From Control
Sodium Azide + EDTA + PMSF

| | Temp. | -15° C | | | | | | | 4° C | | | | | | | 25° C | | | | | | 37° C | | | 45° C |
|---|---|---|---|---|---|---|---|---|---|---|---|---|---|---|---|---|---|---|---|---|---|---|---|---|---|
| | Time | 2W | 1M | 2M | 3M | 4M | 6M | 9M | 2W | 1M | 2M | 3M | 4M | 6M | 9M | 2W | 1M | 2M | 3M | 4M | 2W | 1M | 2M | 2W |
| Angio- | 20 pg | 0 | 1.0% | 2.9% | 1.5% | 1.1% | 1.3% | 3.9% | 1.0% | 2.2% | 2.3% | 1.8% | 3.8% | 0.6% | 3.3% | 2.1% | 0.1% | 0.4% | 1.3% | 1.7% | 2.1% | 2.3% | 0.0% | 1.4% |
| tensin | 50 | 0 | 2.5 | 2.7 | 3.5 | 4.0 | 1.0 | 2.0 | 1.8 | 1.0 | 3.3 | 2.7 | 0.8 | 5.9 | 6.5 | 2.8 | 3.8 | 4.0 | 2.1 | 4.2 | 0.8 | 1.7 | 4.8 | 2.8 |
| stan- | 100 | 0 | 1.2 | 2.8 | 4.3 | 3.6 | 3.7 | 0.0 | 4.8 | 0.8 | 1.4 | 1.1 | 5.0 | 2.4 | 1.9 | 0.3 | 1.0 | 4.6 | 4.0 | 3.6 | 4.9 | 1.0 | 7.8 | 1.2 |
| dards | 200 | 0 | 5.5 | 1.4 | 6.7 | 6.0 | 1.5 | 5.4 | 6.1 | 0.4 | 3.1 | 1.1 | 4.4 | 5.8 | 3.0 | 5.8 | 1.3 | 2.5 | 2.2 | 9.0 | 4.3 | 1.6 | 11.3 | 2.0 |
| | 400 | 0 | 7.2 | 0.4 | 0.9 | 1.8 | 0.8 | 4.5 | 2.5 | 3.0 | 1.9 | 10.6 | 3.6 | 1.6 | 2.8 | 0.4 | 8.2 | 1.8 | 1.8 | 7.7 | 0.5 | 5.0 | 1.2 | 4.1 |
| | 1000 | 0 | 11.3 | 6.7 | 10.9 | 15.0 | 6.1 | 6.0 | 3.7 | 6.4 | 11.2 | 7.3 | 8.9 | 3.0 | 14.4 | 5.6 | 12.6 | 4.1 | 0.0 | 12.1 | 4.9 | 16.5 | 4.7 | 2.3 |

Summary of Stability

| Temp. | Time |
|---|---|
| -15° C | >9 months |
| 4° C | >9 months |
| 25° C | >4 months |
| 37° C | >2 months |
| 45° C | >2 weeks |

Key to Abbreviations:
° C — Degrees Centigrade
EDTA — Ethylenediamine tetraacetate
PMSF — Phenylmethylsulfonyl Fluoride
pg — Picograms ($10^{-12}$ grams)
OD — Zero Day
W — Week
M — Month Stability Specifications: Stability was considered lost if three or more experimental values had a % difference greater than 10% from the corresponding control values.

*% Difference = $\left[ 1 - \left( \dfrac{\text{smaller value}}{\text{larger value}} \right) \right] \times 100$

We claim:

1. A method for increasing the stability of an Angiotensin I or radioiodinated Angiotensin I solution containing buffer and stabilizer systems which method comprises adding to said solution a minor effective stabilizing amount of phenylmethylsulfonyl fluoride.

2. The method of claim 1 wherein from 0.01 to 5 mg of phenylmethylsulfonyl fluoride per ml. of solution is added.

3. The method of claim 1 wherein said stabilizer system comprises sodium azide and the sodium salt of ethylenediamine tetraacetic acid.

4. The method of claim 1 wherein said solution is heated to 55°–60° C. after addition of said phenylmethylsulfonyl fluoride.

5. An Angiotensin I composition of enhanced stability comprising the following amounts of each constituent per ml. of buffer
   (a) 0.1 ng to 10 mg of Angiotensin I;
   (b) 0.1 to 10 mg of sodium azide;
   (c) 0.1 to 2 mg of the sodium salt of ethylenediamine tetraacetic acid;
   (d) 0.1 to 50 mg of a carrier protein; and
   (e) 0.01 to 5 mg of phenylmethylsulfonyl fluoride.

6. The composition of claim 5 wherein said buffer is 0.1 M Tris, pH 7.5.

7. The composition of claim 5 where said carrier protein is bovine serum albumin.

8. A radioiodinated Angiotensin I wherein said composition contains the following amounts of each constituent per ml of buffer:
   (a) 1 pg to 1000 ng of radioiodinated Angiotensin I;
   (b) 0.1 to 10 mg of sodium azide;
   (c) 0.1 to 2 mg of the sodium salt of ethylenediamine tetraacetic acid;
   (d) 0.1 to 50 mg of a carrier protein; and
   (e) 0.1 to 5 mg of phenylmethylsulfonyl fluoride.

9. The composition of claim 8 wherein said buffer is 0.1 M Tris, pH 9.0.

10. The composition of claim 8 where said carrier protein is bovine serum albumin.

* * * * *